(12) United States Patent
Gundberg (10) Patent No.: US 9,943,293 B2
(45) Date of Patent: Apr. 17, 2018

(54) HANDHELD TISSUE SAMPLE EXTRACTION DEVICE

(71) Applicant: TeesuVac ApS, Aarhus N (DK)

(72) Inventor: Tomas Gundberg, Viby Sjælland (DK)

(73) Assignee: TeesuVac ApS, Aarhus N (DK)

( * ) Notice: Subject to any disclaimer, the term of this patent is extended or adjusted under 35 U.S.C. 154(b) by 171 days.

(21) Appl. No.: 14/357,082

(22) PCT Filed: Nov. 9, 2012

(86) PCT No.: PCT/DK2012/050412
§ 371 (c)(1),
(2) Date: May 8, 2014

(87) PCT Pub. No.: WO2013/068017
PCT Pub. Date: May 16, 2013

(65) Prior Publication Data
US 2015/0057571 A1 Feb. 26, 2015

(30) Foreign Application Priority Data

Nov. 9, 2011 (DK) .................................. 2011 00876
Jan. 30, 2012 (DK) .................................. 2012 00853

(51) Int. Cl.
*A61B 10/00* (2006.01)
*A61B 10/02* (2006.01)
*A61B 17/30* (2006.01)

(52) U.S. Cl.
CPC ...... *A61B 10/0275* (2013.01); *A61B 10/0283* (2013.01); *A61B 2010/0208* (2013.01); *A61B 2017/306* (2013.01)

(58) Field of Classification Search
CPC ............ A61B 10/0283; A61B 10/0275; A61B 2010/0208
(Continued)

(56) References Cited

U.S. PATENT DOCUMENTS 4,010,959 A * 3/1977 Smith, III .............. G11B 33/06
369/198
5,425,376 A 6/1995 Banys et al.
(Continued)

FOREIGN PATENT DOCUMENTS

CN 101442942 A 5/2009
DE 19848513 A1 8/2000
(Continued)

OTHER PUBLICATIONS

Notification of the First Office Action dated Jul. 31, 2015 from The State intellectual Property Office of the People's Republic of China for CN Application No. 2012800664586, including Search Report (6 pages).

*Primary Examiner* — Daniel Cerioni
(74) *Attorney, Agent, or Firm* — Peter A. Nieves; Sheehan Phinney Bass & Green PA (57) ABSTRACT

A handheld device for extracting tissue samples includes a needle arrangement and control arrangement. The needle arrangement has a cutting needle, a sample extraction needle, and a first end for inserting into tissue. The cutting needle has a cutting edge for cutting the tissue sample. The sample extraction needle has a side opening for receiving the tissue. The control arrangement has a vacuum chamber in fluid communication with the sample extraction needle. The vacuum chamber has a first member and a second member that move relative to each other. The first member is mechanically connected to the cutting needle. The handheld device is configured so that movement between the first and second members to increase volume of the vacuum chamber thereby reduces pressure in the sample extraction needle, induces movement between the cutting needle and the sample extraction needle to expose the side opening.

20 Claims, 7 Drawing Sheets

(58) Field of Classification Search
USPC .................................................. 600/566
See application file for complete search history.

(56) References Cited

U.S. PATENT DOCUMENTS

| | | | |
|---|---|---|---|
| 5,527,332 A | 6/1996 | Clement | |
| 5,560,373 A | 10/1996 | De Santis | |
| 5,617,874 A | 4/1997 | Baran | |
| 5,713,368 A | 2/1998 | Leigh | |
| 5,797,883 A | 8/1998 | Prince | |
| 5,817,033 A | 10/1998 | deSantis et al. | |
| 5,893,862 A | 4/1999 | Pratt et al. | |
| 5,928,164 A | 7/1999 | Burbank et al. | |
| 5,944,673 A | 8/1999 | Gregoire et al. | |
| 6,077,230 A | 6/2000 | Gregoire et al. | |
| 6,210,420 B1 | 4/2001 | Mauze et al. | |
| 6,491,645 B1 | 12/2002 | Gaber | |
| 6,656,132 B1 | 12/2003 | Oucchi et al. | |
| 6,730,045 B2 | 5/2004 | Finer | |
| 6,858,014 B2 | 2/2005 | Damarati | |
| 6,918,880 B2 | 7/2005 | Brookner et al. | |
| 6,981,949 B2 | 1/2006 | Hibner et al. | |
| 7,186,252 B2 | 3/2007 | Nobis et al. | |
| 7,189,206 B2 | 3/2007 | Quick et al. | |
| 7,229,439 B2 | 6/2007 | Burbank et al. | |
| 7,311,672 B2 | 12/2007 | Van Bladell | |
| 7,517,321 B2 | 4/2009 | McCullough et al. | |
| 7,645,239 B2 | 1/2010 | Heske et al. | |
| 7,794,409 B2 | 9/2010 | Damarati | |
| 7,819,819 B2 | 10/2010 | Quick et al. | |
| 7,828,747 B2 | 11/2010 | Heske et al. | |
| 7,918,803 B2 | 4/2011 | Ritchart et al. | |
| 7,959,580 B2 | 6/2011 | McCullough et al. | |
| 7,981,049 B2 | 7/2011 | Ritchie et al. | |
| 7,988,642 B2 | 8/2011 | Hardin | |
| 8,012,102 B2 | 9/2011 | McCullough et al. | |
| 8,016,772 B2 | 9/2011 | Heske et al. | |
| 8,048,003 B2 | 11/2011 | Nicoson | |
| 8,052,614 B2 | 11/2011 | Heske et al. | |
| 8,052,615 B2 | 11/2011 | Videbæk et al. | |
| 8,109,885 B2 | 2/2012 | Heske et al. | |
| 8,147,487 B2 | 4/2012 | Burbank et al. | |
| 8,157,744 B2 | 4/2012 | Videbæk et al. | |
| 8,162,851 B2 | 4/2012 | Heske et al. | |
| 8,231,544 B2 | 7/2012 | Mark | |
| 8,251,917 B2 | 8/2012 | Almazan | |
| 8,262,585 B2 | 9/2012 | Thompson et al. | |
| 8,267,868 B2 | 9/2012 | Taylor et al. | |
| 8,287,465 B2 | 10/2012 | Hardin et al. | |
| 8,343,071 B2 | 1/2013 | Shabaz | |
| 8,357,103 B2 | 1/2013 | Mark | |
| 8,366,636 B2 | 2/2013 | Videbæk et al. | |
| 8,376,957 B2 | 2/2013 | Hibner et al. | |
| 8,430,827 B2 | 4/2013 | Nicoson | |
| 8,486,097 B2 | 7/2013 | Mark et al. | |
| 8,568,335 B2 | 10/2013 | Monson et al. | |
| 8,702,621 B2 | 4/2014 | McCullough et al. | |
| 8,702,622 B2 | 4/2014 | McCullough et al. | |
| 8,721,563 B2 | 5/2014 | Taylor et al. | |
| 8,728,003 B2 | 5/2014 | Taylor et al. | |
| 8,728,004 B2 | 5/2014 | Taylor et al. | |
| 8,771,200 B2 | 7/2014 | Thompson et al. | |
| 8,845,547 B2 | 9/2014 | Heske et al. | |
| 8,864,680 B2 | 10/2014 | Videbæk et al. | |
| 8,915,864 B2 | 12/2014 | Quick et al. | |
| 8,926,527 B2 | 1/2015 | Jorgensen et al. | |
| 8,951,208 B2 | 2/2015 | Almazan | |
| 9,072,502 B2 | 7/2015 | Heske et al. | |
| 9,072,506 B1 | 7/2015 | Seiger | |
| 9,161,743 B2 | 10/2015 | McCullough et al. | |
| 9,421,002 B2 | 8/2016 | Heske et al. | |
| 9,439,632 B2 | 9/2016 | Almazan | |
| 9,456,809 B2 | 10/2016 | Jorgensen et al. | |
| 9,566,045 B2 | 2/2017 | Videbaek et al. | |
| 2002/0111563 A1 | 8/2002 | Hall | |
| 2002/0120212 A1 | 8/2002 | Ritchart | |
| 2004/0054299 A1* | 3/2004 | Burdorff | A61B 10/0275 600/564 |
| 2004/0167427 A1 | 8/2004 | Quick et al. | |
| 2005/0033197 A1 | 2/2005 | Cottler | |
| 2006/0293610 A1 | 12/2006 | Heske | |
| 2007/0106176 A1 | 5/2007 | Mark et al. | |
| 2007/0161925 A1 | 7/2007 | Quick | |
| 2007/0179343 A1 | 8/2007 | Shelokov | |
| 2007/0208272 A1 | 9/2007 | Voegele | |
| 2007/0213631 A1 | 9/2007 | Kondo | |
| 2008/0103412 A1 | 5/2008 | Chin | |
| 2008/0200833 A1 | 8/2008 | Hardin et al. | |
| 2008/0319342 A1 | 12/2008 | Shabaz | |
| 2009/0143698 A1 | 6/2009 | Janssens | |
| 2009/0177115 A1 | 7/2009 | Zambelli | |
| 2009/0204021 A1 | 8/2009 | Shabaz et al. | |
| 2010/0094166 A1 | 4/2010 | Kraemer et al. | |
| 2010/0106053 A1* | 4/2010 | Videbaek | A61B 10/0096 600/564 |
| 2010/0152610 A1 | 6/2010 | Parihar et al. | |
| 2010/0152612 A1 | 6/2010 | Headley, Jr. | |
| 2011/0152715 A1 | 6/2011 | Delap et al. | |
| 2011/0208089 A1 | 8/2011 | Sundheimer et al. | |
| 2011/0224576 A1 | 9/2011 | Jackson | |
| 2012/0010527 A1 | 1/2012 | Sundheimer et al. | |
| 2012/0071787 A1* | 3/2012 | Reuber | A61B 10/0275 600/567 |
| 2012/0215231 A1 | 8/2012 | Wesley | |
| 2012/0253225 A1 | 10/2012 | Boutaghou et al. | |
| 2013/0144186 A1 | 6/2013 | Furlong | |
| 2013/0197394 A1 | 8/2013 | Mark et al. | |
| 2013/0289441 A1 | 10/2013 | Videbaek | |
| 2013/0324882 A1 | 12/2013 | Mescher | |
| 2013/0331733 A1 | 12/2013 | Plishka et al. | |
| 2014/0039344 A1 | 2/2014 | Quick | |
| 2015/0080760 A1 | 3/2015 | Quick et al. | |
| 2016/0262733 A1 | 9/2016 | Schlarb | |
| 2016/0317133 A1 | 11/2016 | Orts et al. | |
| 2016/0367230 A1 | 12/2016 | Almazan | |

FOREIGN PATENT DOCUMENTS

| | | |
|---|---|---|
| DE | 100 59 264.3 | 8/2001 |
| DE | 100 26 303.8 A1 | 2/2002 |
| DE | 102 41 084.4 A1 | 3/2004 |
| DE | 603 14 109.9 | 2/2005 |
| DE | 60 2004 010 756.5 T2 | 3/2005 |
| DE | 20 2004 012 970.1 U1 | 1/2006 |
| EP | 0647429 | 4/1995 |
| EP | 0780089 A1 | 6/1997 |
| EP | 0870486 A1 | 10/1998 |
| EP | 1518498 A1 | 3/2005 |
| EP | 1792574 A1 | 6/2007 |
| EP | 1829487 A1 | 9/2007 |
| EP | 1889572 | 2/2008 |
| EP | 2078496 A1 | 7/2009 |
| EP | 2196153 | 6/2010 |
| EP | 2260767 | 12/2010 |
| EP | 2389868 | 11/2011 |
| EP | 2407111 | 1/2012 |
| EP | 2649946 | 10/2013 |
| EP | 2954847 | 12/2015 |
| FR | 2715056 A1 | 7/1995 |
| JP | 20081000821 A | 5/2008 |
| WO | 9956628 A1 | 11/1999 |
| WO | 03086198 | 4/2003 |
| WO | 03077767 | 9/2003 |
| WO | 2004075719 | 9/2004 |
| WO | 2004086977 | 10/2004 |
| WO | 2005063126 | 7/2005 |
| WO | 2006005342 | 1/2006 |
| WO | 2006005343 | 1/2006 |
| WO | 2006005344 | 1/2006 |
| WO | 2006005345 | 1/2006 |
| WO | 2006017400 | 2/2006 |
| WO | 2006063770 A1 | 8/2006 |
| WO | 2007021903 | 2/2007 |
| WO | 2007021905 | 2/2007 |

(56) References Cited

FOREIGN PATENT DOCUMENTS

| | | |
|---|---|---|
| WO | WO2007019445 A1 | 2/2007 |
| WO | WO2007110812 A1 | 10/2007 |
| WO | 2008024684 | 2/2008 |
| WO | WO 2008/024684 | 2/2008 |
| WO | WO2008106583 A1 | 9/2008 |
| WO | WO 2010/071746 | 6/2010 |
| WO | 2010091048 | 8/2010 |
| WO | 2011002701 A1 | 1/2011 |
| WO | 2011035125 A1 | 3/2011 |
| WO | 2011097494 A2 | 8/2011 |
| WO | 2012018461 A2 | 2/2012 |
| WO | WO/2012/015801 | 2/2012 |
| WO | WO2013109753 | 7/2013 |
| WO | 2013158072 A1 | 10/2013 |
| WO | 2013181005 A1 | 12/2013 |
| WO | 2013184466 A1 | 12/2013 |
| WO | 2014004163 A1 | 1/2014 |
| WO | 2014153410 | 9/2014 |
| WO | 2004086978 | 10/2014 |
| WO | 2015069223 | 5/2015 |

\* cited by examiner

HANDHELD TISSUE SAMPLE EXTRACTION DEVICE

FIELD OF THE INVENTION

The present invention relates to a handheld device for extracting tissue samples from tissue.

BACKGROUND OF THE INVENTION

It is known to extract tissue samples from tissue using various devices. Such a device is described in US patent application US 2007/106176 A1.

However, there may be several problems associated with such known devices. It is therefore an object of the invention to provide a simple yet efficient handheld device for extraction of tissue samples.

BRIEF DESCRIPTION OF THE INVENTION

The invention relates to a handheld device for extraction of tissue samples, comprising a needle arrangement and a control arrangement, said needle arrangement comprising a cutting needle and a sample extraction needle, said needle arrangement having a first end for inserting into tissue, said cutting needle comprising a cutting edge for cutting said tissue sample from said tissue, said sample extraction needle comprising a side opening for receiving said tissue, said control arrangement comprising a vacuum chamber in fluid communication with said sample extraction needle, the vacuum chamber comprising a first member and a second member, said first and second members being adapted to move relative to each other, wherein said first member is mechanically connected to said cutting needle, and wherein said handheld device is configured so that a movement between said first member and said second member to increase the volume of said vacuum chamber thereby reducing the pressure in said sample extraction needle induces a movement between said cutting needle and said sample extraction needle to expose said side opening of said sample extraction needle.

An advantage of the invention may be that by said first member and said cutting needle being connected, a minimum of driving force arrangement is required for operating said handheld device. I.e. only one driving arrangement is required to move the first member and the cutting needle collectively.

Furthermore, an important advantage of the invention may be that by moving said cutting needle along said longitudinal axis away from said sample extraction needle end and thereby exposing the side opening of the sample extraction needle, the vacuum chamber expands due to the first member being connected to the cutting needle. Therefore, and since the vacuum chamber is in fluid communication with the needle, the expanding vacuum chamber, having a decreasing pressure, facilitates suction of tissue in the vicinity of the side opening of the sample extraction needle into the tissue sample chamber. Thereby, the handheld device and the tissue are ready for the cutting needle to cut the tissue sample from the tissue, which may be performed by said cutting needle moving back over said side opening.

A further advantage of the invention may be that by reducing the pressure in the vacuum chamber being in fluid communication with the sample extraction needle while exposing the side opening of the sample extraction needle, a vacuum assisted handheld device is obtained, i.e. a handheld device which uses vacuum to suck tissue into the sample extraction needle which may then subsequently be cut off to give a tissue sample.

Thereby, a simple yet efficient handheld device for extracting tissue samples, i.e. for performing biopsies, is obtained.

In the present context it should be understood that side opening is an opening in the side of the inner sample extraction needle allowing a part of surrounding tissue to move through said side opening into a tissue receiving chamber of the sample extraction needle. This movement of the tissue into the tissue receiving chamber is facilitated at least partly by the vacuum in the vacuum chamber being in fluid communication with said needle arrangement, and more specifically with the tissue sample chamber of the sample extraction needle. Thereby, a vacuum assisted process for extraction of tissue sample is achieved by means of said handheld device.

It is to be understood in relation to the above that the cutting edge of the cutting needle is adapted for cutting through tissue, i.e. to separate the tissue in the tissue sample chamber from the rest of the surrounding tissue by cutting it off, thereby obtaining a tissue sample.

In the present context, said sample extraction needle is hollow so as to facilitate vacuum from the control arrangement to the tissue sample chamber and the side opening. Also, the cutting needle and the sample extraction needle both have openings corresponding to each other thereby facilitating the transfer of vacuum from the vacuum chamber to the tissue sample chamber and the side opening.

It is to be understood that the control arrangement typically may be a handle comprising a vacuum chamber and arrangements for controlling the movement of the cutting needle and for controlling the vacuum chamber. However, of course the control arrangement may be designed in various other ways allowing control of the cutting needle and the vacuum chamber.

According to an embodiment of the invention, the cutting needle is an outer needle surrounding the sample extraction needle along at least a part of the length of the cutting needle and/or the inner sample extraction needle.

According to an embodiment of the invention, said first member is connected to said cutting needle so as to increase the volume of said vacuum chamber and expose said side opening when moving said cutting needle along the longitudinal axis of the needle arrangement away from said first end of said needle arrangement.

According to an embodiment, said first and second members are adapted to move relative to each other so as to increase the volume of said vacuum chamber with a movement of said cutting needle relative to said sample extraction needle in a direction away from said first end of said needle arrangement thereby exposing said side opening of said sample extraction needle.

According to an embodiment, said handheld device is configured so that a movement between said cutting needle and said sample extraction needle to expose said side opening of said sample extraction needle is coupled to a movement between said first member and said second member to increase the volume of said vacuum chamber, thereby reducing the pressure in said sample extraction needle due to said first member being mechanically connected to said cutting needle.

According to an embodiment of the invention, said first member is a piston and said second member is a cylinder.

According to the above embodiment, the piston is mechanically connected to the cutting needle, thereby coupling the movement of the two together. Preferably the piston and the cutting needle are connected such that they move together along the longitudinal axis of the needle arrangement, but may rotates freely about the same longitudinal axis relative to each other.

According to an embodiment of the invention, said first member is a cylinder and said second member is a piston.

According to the above embodiment, the cylinder is mechanically connected to the cutting needle, thereby coupling the movement of the two together. Preferably the cylinder and the cutting needle are connected such that they move together in the direction along the longitudinal axis of the needle arrangement, but may rotate freely about the same longitudinal axis relative to each other.

According to an embodiment of the invention, said movement between said first member and said second member to increase the volume of said vacuum chamber is in a direction along the longitudinal axis of the needle arrangement.

According to an embodiment of the invention, said first member is fixated to said cutting needle.

According to the above embodiment, the first member is fixated to the cutting needle, i.e. mechanically fixated. In some embodiments the fixation is in the direction parallel to the longitudinal axis of the needle arrangement, i.e. the first member and the cutting needle will move together in this direction, but the two may rotate about the longitudinal axis independently of each other. However, in other embodiments, the two may be totally fixated to each other for every direction of movement and rotation.

According to an embodiment of the invention, the vacuum chamber surrounds at least a part of said needle arrangement.

Thereby, the fluid communication between from the vacuum chamber to the sample extraction needle may be facilitated in a simple and efficient way, e.g. by means of through-holes and/or slits in the cutting needle and in the sample extraction needle.

According to an embodiment of the invention, the vacuum chamber is centered about the longitudinal axis of the needle arrangement.

According to an embodiment of the invention, the cutting needle is an outer needle surrounding the sample extraction needle being an inner needle.

In the context of the above embodiment it is to be understood that by said cutting needle surrounding said sample extraction needle is meant that may surround the sample extraction needle or a part thereof depending on the relative position of the two. According to an embodiment, it may be understood that the outer cutting needle may be referred to as a cannula, where inner sample extraction needle may be referred to as e.g. a trocar needle or a trocar-like needle.

According to an embodiment of the invention, the relative movement of said first and second members are driven by second driving arrangement.

According to an embodiment of the invention, said second driving arrangement comprise a second spring.

In relation to the above embodiment the second spring may extend from a part of the first member and a part of the second member. Thereby, it facilitates relative movement between the two members. In embodiments where e.g. the first member is a piston and the second member is a cylinder, the second spring may be fitted to the piston near the end the piston facing away from the first end of the needle arrangement, while the second end of the second spring may be fitted to the end of the cylinder facing towards the first end of the needle arrangement. Preferably, then the spring is a compressing spring, i.e. it is compressed when the piston is fully inserted into the cylinder, and is less compressed when the piston is moved as far as possible out of the cylinder. Therefore, the second driving arrangement is preferably a spring that can be compressed or stretched, i.e. potential energy can be stored in the spring and converted into kinetic energy when released, e.g. by the movement of pins to release one or more parts affected by the biasing force of the spring, thereby initiating movement driven by the spring.

According to an embodiment of the invention, said cutting needle has a bevelled end.

An advantage of the above embodiment is that the cutting needle may have improved cutting characteristics, e.g. when performing an oscillatory rotation during cutting.

According to an embodiment of the invention, said vacuum chamber is adapted to build up a vacuum before the side opening is exposed.

An advantage of the above embodiment is that immediately when the side opening starts being just partly exposed, there is already a vacuum in the vacuum chamber, resulting in the tissue immediately being sucked into the tissue sample chamber.

According to an embodiment of the invention, said second member is adapted to perform a movement along the longitudinal axis of the needle arrangement towards the first end of the needle arrangement thereby increasing the volume of the vacuum chamber and building up a vacuum before the side opening is exposed.

In relation to the above it is to be understood that said second member may be a piston or a cylinder depending on the nature of the first member, such that the first and second members together constitute are a piston and a cylinder.

According to an embodiment of the invention, said handheld device comprises first driving arrangement for driving a movement of said second member along the longitudinal axis of the needle arrangement towards the first end of the needle arrangement.

According to an embodiment of the invention, said first driving arrangement comprise a first spring.

In relation to the above embodiment, it may in some embodiments be preferred that the first spring is connected to the second member and a casing of the control arrangement. Thereby, the first spring may move the second member towards the first end of the needle arrangement over at least some distance without moving said first member. Furthermore, when moving said second member towards the first end of the needle arrangement causes the first member to move along due to e.g. a coupling between the two members preventing them from moving out of contact with each other, the first spring may facilitate movement of the two members together relative to the rest of the control arrangement. Therefore, the first driving arrangement is preferably a spring that can be compressed or stretched, i.e. potential energy can be stored in the spring and converted into kinetic energy when released, e.g. by the movement of pins to release one or more parts affected by the biasing force of the spring, thereby initiating movement driven by the spring.

According to an embodiment of the invention, said first and second members are adapted to move together in a direction along the longitudinal axis of the needle arrangement in a direction towards the first end of the needle arrangement while being substantially stationary relative to each other, wherein said cutting needle connected to said first member and said sample extraction needle are adapted for moving relative to each other along the longitudinal axis of said needle arrangement from a first to a second relative position, wherein at least a part of said side opening is exposed in said first relative position, and wherein said side opening of said sample extraction needle is substantially covered in said second relative position, thereby cutting said tissue sample from said tissue.

An advantage of the above embodiment is by moving said first and second members together the volume of the vacuum chamber is substantially constant while the cutting needle moves over the sample extraction needle and performs a cutting action by cutting tissue extending through the side opening into the tissue sample chamber from the rest of the tissue to give a tissue sample. Thereby, the suction in the inner sample extraction needle, which sucks a part of the surrounding tissue into the sample extraction chamber, and which is facilitated by the vacuum chamber is substantially constant through the cutting process.

According to an embodiment of the invention, said movement from said first relative position to said second relative position comprises an oscillatory rotation of said cutting needle relative to said sample extraction needle about the longitudinal axis of the needle arrangement, where said oscillatory rotation comprises at least a first relative rotation and a second relative rotation, where the first and second relative rotations have different oscillatory velocities.

In the present context of the above embodiment, said oscillatory rotation is to be a rotation at different oscillatory velocities, e.g. different oscillatory velocities for the same velocity of the cutting needle between said first and second relative positions. In various examples the two different oscillation velocities may or may not be in opposite rotational direction, e.g. in one example embodiment the two rotational velocities may be in the same rotational direction, but at various numerical values of the velocities, while in another example embodiment one of the rotational velocities may be zero, i.e. the cutting needle rotates only for a portion of the way between said first and second relative positions.

According to an embodiment of the invention, said movement from said first relative position to said second relative position comprises an oscillatory rotation of said cutting needle relative to said sample extraction needle about the longitudinal axis of the needle arrangement, where said oscillatory rotation comprises at least a first relative rotation and a second relative rotation, where the first and second relative rotations have opposite rotational directions.

In the present context of the above embodiment, said oscillatory rotation is to be understood as a rotation about the longitudinal axis of the needle arrangement. Moreover, it is to be understood as a rotation that changes rotational direction at least once and possibly several times, e.g. by switching rotational direction for each 360° rotation or for each 180°, 90°, 45°, or 20° of rotation or by other angular intervals.

An advantage of the above embodiment is that by said cutting needle performing a oscillatory rotation when moving from said first and to said second relative position, the tissue cutting efficiency of the cutting edge of the cutting needle is substantially increased compared to a non-rotating cutting needle, while at the same performing said oscillatory rotation having one or more rotations in each rotational direction about said longitudinal axis of the needle arrangement so that the net sum of these one or more rotations in each rotational direction is small compared to the sum of the numeric rotations, preferably such that the net sum of the rotations is less than 360°, such as less than 180°, such as less than 90°, such as less than 45°, such as less than 20°.

A further advantage of the invention is that since the cutting needle has a net sum of rotations being much smaller compared to the sum of the numeric rotations, it is avoided that the cutting needle winds up part of the tissue or other parts of material inside the body of the person from whom this tissue sample is extracted, such as a tendon. Such winding up of the e.g. tissue or a tendon may be extremely painful and may furthermore cause the cutting needle to be stuck in the person. Thereby a less painful sample extraction can be performed by the easy-to-use handheld device.

According to an embodiment of the invention, the handheld device comprises vacuum removal arrangement for removing the vacuum when said cutting needle has reached the second relative position thereby substantially covering said side opening of said sample extraction needle.

By removing the vacuum when the cutting needle covers the side opening of the sample extraction needle, it is avoided that the tissue sample which has now been cut from the tissue moves to much up the inner space of the sample extraction needle.

According to an embodiment of the invention, the vacuum removal arrangement comprises a valve.

According to and embodiment of the invention, the valve may e.g. be positioned such that it removes the vacuum by bringing the vacuum chamber into fluid contact with the surrounding, e.g. when said second member reaches a position closest to the first end of the needle arrangement, i.e. when the cutting needle has moved back over the side opening.

According to an embodiment of the invention, the control arrangement furthermore comprises a charging arrangement for charging said first and second driving arrangements.

According to an embodiment of the invention, the charging arrangement is a ring and a string.

In embodiments where the first and second driving arrangements are a first and second spring, the charging arrangement may e.g. comprise a ring and a string connected to the ring and to the first and/or second members such that when pulling the ring the first and second members move to their positions bringing the first and second springs into compressed or stretched mode, i.e. storing energy for the sample extraction sequence in the springs. Alternatively, the charging arrangement may comprise a trigger, which can be operated by one or more fingers of the user of the handheld device, to activate one or more times in order to store sufficiently energy in the driving arrangements, such as the springs. Yet another alternative solution may comprise an electrically driven motor, preferably connected to a battery, which can bring the driving arrangements, such as the springs, into loaded mode.

According to an embodiment of the invention, the sample extraction needle may be removed from the rest of the handheld device so as to remove extracted tissue samples.

Alternative, the tissue samples may be removed by other means, e.g. to an internal tissue sample storage chamber inside the control arrangement or by removing the entire needle arrangement from the tissue and extracting the tissue sample through the side opening of the sample extraction needle.

The invention furthermore relates to a handheld device for extraction of tissue samples, comprising a needle arrangement and control arrangement, said needle arrangement comprising a cutting needle and a sample extraction needle, said needle arrangement having a first end for inserting into tissue, said cutting needle comprising a cutting edge for cutting said tissue sample from said tissue, said sample extraction needle comprising a side opening for receiving said tissue, wherein said cutting needle and said sample extraction needle are adapted for moving relative to each other in a direction along the longitudinal axis of the needle arrangement from a first to a second relative position, wherein at least a part of said side opening is exposed in said first relative position, and wherein said side opening of said sample extraction needle is substantially covered in said second relative position, and wherein said movement from said first relative position to said second relative position comprises an oscillatory rotation of said cutting needle relative to said sample extraction needle about the longitudinal axis of the needle arrangement, where said oscillatory rotation comprises a first relative rotation and a second relative rotation, where the first and second relative rotations have different oscillatory velocities.

In the present context of the above embodiment, said oscillatory rotation is to be a rotation at different oscillatory velocities, e.g. different oscillatory velocities for the same velocity of the cutting needle between said first and second relative positions. In various examples the two different oscillation velocities may or may not be in opposite rotational direction, e.g. in one example embodiment the two rotational velocities may be in the same rotational direction, but at various numerical values of the velocities, while in another example embodiment one of the rotational velocities may be zero, i.e. the cutting needle rotates only for a portion of the way between said first and second relative positions.

According to an embodiment of the invention, the first and second relative rotations have opposite rotational directions.

In the present context, said oscillatory rotation is to be understood as a rotation about the longitudinal axis of the needle arrangement. Moreover, it is to be understood as a rotation that changes rotational direction at least once and possibly several times, e.g. by switching rotational direction for each 360° rotation or for each 180°, 90°, 45°, or 20° of rotation or by other angular intervals.

An advantage of the invention is that by said cutting needle performing a oscillatory rotation when moving from said first and to said second relative position, the tissue cutting efficiency of the cutting edge of the cutting needle is substantially increased compared to a non-rotating cutting needle, while at the same performing said oscillatory rotation having one or more rotations in each rotational direction about said longitudinal axis of the needle arrangement so that the net sum of these one or more rotations in each rotational direction is small compared to the sum of the numeric rotations, preferably such that the net sum of the rotations is less than 360°, such as less than 180°, such as less than 90°, such as less than 45°, such as less than 20°.

A further advantage of the invention is that since the cutting needle has a net sum of rotations being much smaller compared to the sum of the numeric rotations, it is avoided that the cutting needle winds up part of the tissue or tendon or other parts of material inside the body of the person from whom this tissue sample is extracted. Such winding up of the e.g. tissue or tendon may be extremely painful and may furthermore cause the cutting needle to be stuck in the person. Thereby a less painful sample extraction can be performed by the easy-to-use handheld device.

According to an embodiment of the invention, the oscillation control arrangement may comprise an oscillating ridge connected to e.g. the cutting needle and controlled by two pins on the control arrangement. Of course the ridge may also be on the control arrangement and the pins connected to the cutting needle. In another embodiment, the oscillation control arrangement may comprise an oscillating channel in which a pin is guided along. The channel may then be a part of the control arrangement, while the pin may be connected to the cutting needle, or opposite.

According to an embodiment of the invention, the above described handheld device may be combined with any other embodiments of the invention.

FIGURES

The invention will now be described with reference to the drawings, where.

DESCRIPTION OF THE INVENTION

Figure 1:
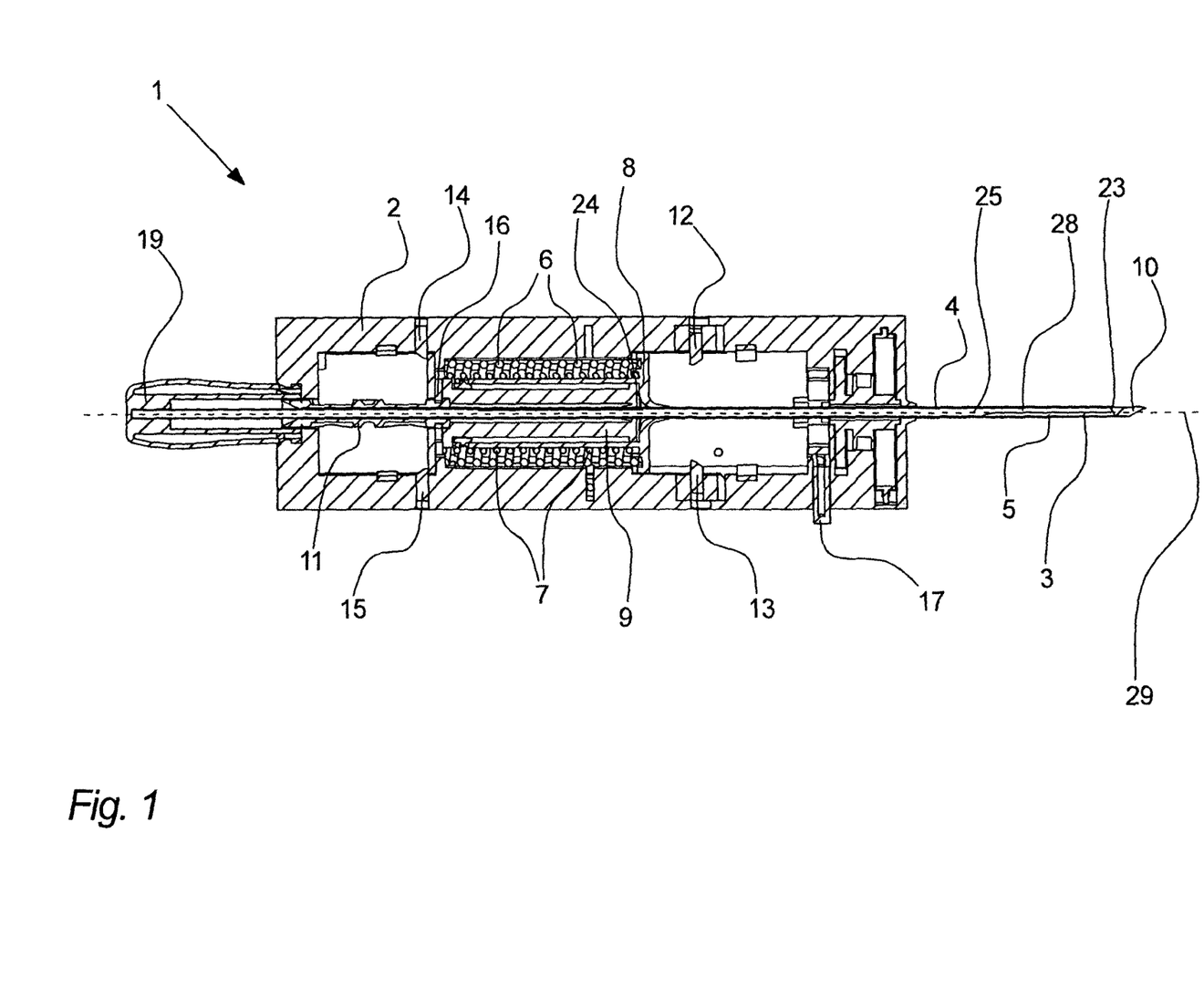
FIG. 1 illustrates a handheld device according to an embodiment of the invention.
Figure 2:
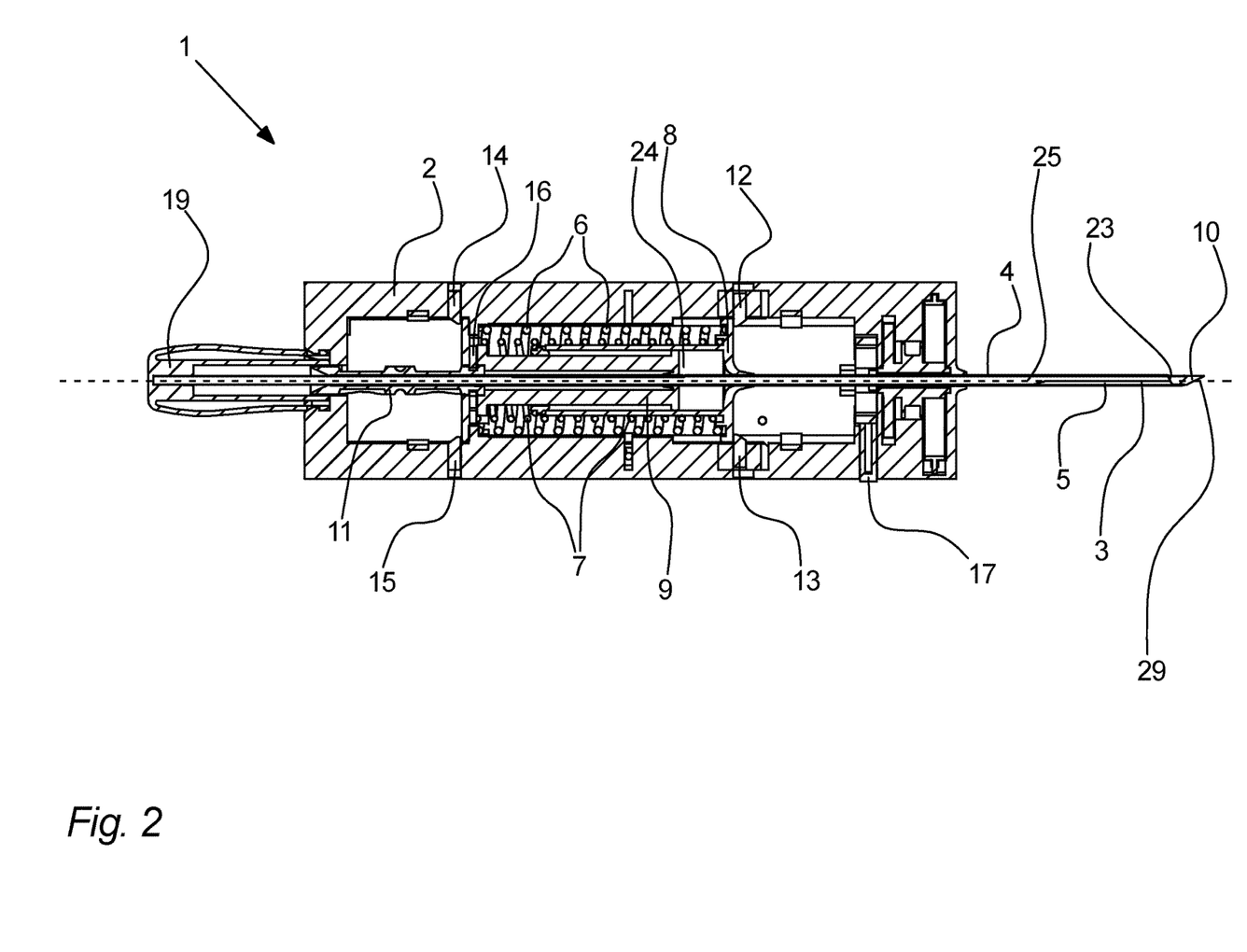
FIG. 2 illustrates a handheld device according to an embodiment of the invention.

Referring to FIG. 1, a handheld device 1 for extraction of tissue samples 27 is illustrated in a cross-sectional view according to an embodiment of the invention. The handheld device 1 comprises control arrangement 2 and a needle arrangement 25. The needle arrangement 25 comprises an inner sample extraction needle 3 and an outer cutting needle 4. The inner sample extraction needle 3 has an outer diameter corresponding to the inner diameter of the outer cutting needle 4 so that the two may move relative to each other in a direction along a longitudinal axis 29 of the needle arrangement 25. The inner sample extraction needle 3 comprises a side opening 5 into a tissue sample chamber 26 and a beveled needle end 10. The outer cutting needle 4 has a cutting edge 23, which may be beveled as in FIG. 1, or may in alternative embodiments constitute an orthogonal cut-through of the outer cutting needle 4. The control arrangement 2 comprises a vacuum chamber 24, which comprises a piston 9 and a cylinder 8. The control arrangement 2 furthermore comprises a first spring 6 and a second spring 7 for supplying driving force for movement of the piston 9 and the cylinder 8. The springs 6, 7 are compression springs. The control arrangement 2 furthermore comprises a first pin 12, a second pin 13, a third pin 14, and a fourth pin 15 for controlling the movement of the piston 9 and the cylinder 8. Finally, the control arrangement 2 comprises a start button 17 for initiating the tissue sample extraction as will be described in relation to FIGS. 1-5. During use of the handheld device 1 for extraction of tissue samples 27, the needle arrangement 5 is inserted into the tissue 30 in this configuration.

The inner sample extraction needle 3 is connected to a handle 19 at the end opposite the beveled needle end 10. The outer cutting needle 4 is connected to oscillation control arrangement 11, which is connected to the piston 9 by a first connection arrangement 16. The vacuum chamber 24 is in fluid communication with the inner sample extraction needle 3, by means of e.g. openings in the outer cutting needle 4 and the inner sample extraction needle 3. Such openings may e.g. be slits positioned such that the fluid communication is upheld for any position and orientation of the outer cutting needle 4 and of the inner sample extraction needle 3 during a sampled extraction cycle. In the configuration that is illustrated on FIG. 1, the first and second springs 6, 7 are in a tensioned mode, i.e. they are compressed on the direction parallel to the longitudinal direction of the spring relative to their equilibrium position. The tissue sample extraction cycle is initiated by pressing the start button 17, which causes the cylinder 8 to be released by pins (not shown) and to move along towards the first end of the control arrangement 2 until it meets the first and second pins 12, 13. Thereby, a vacuum is build up in the vacuum chamber 24. This situation is illustrated on FIG. 2 in a cross-sectional view, where the start button 17 is pushed into the control arrangement 2 and the cylinder 8 has moved into contact with the first and second pins 12, 13.

Figure 3:
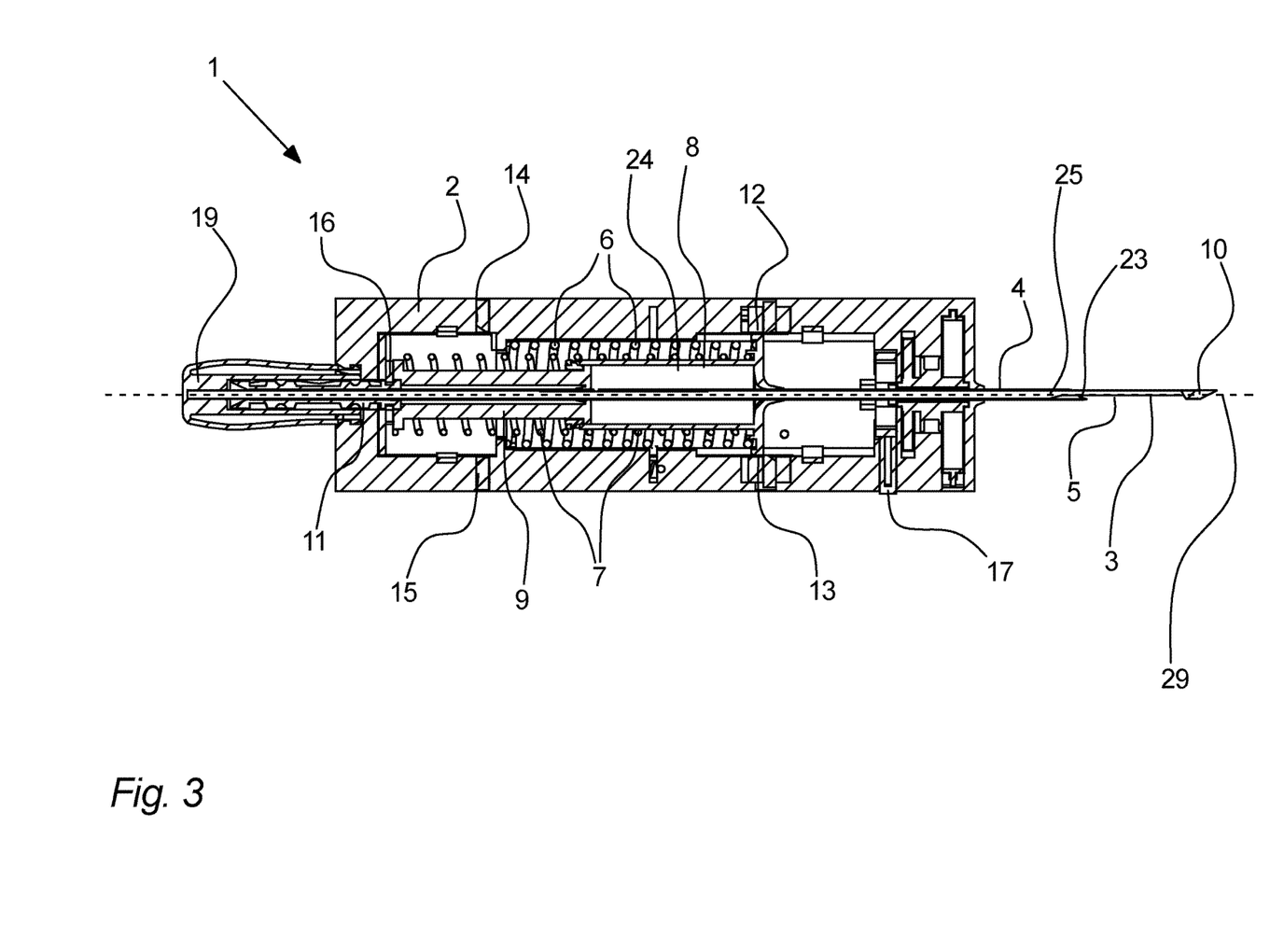
FIG. 3 illustrates a handheld device according to an embodiment of the invention.
Figure 4:
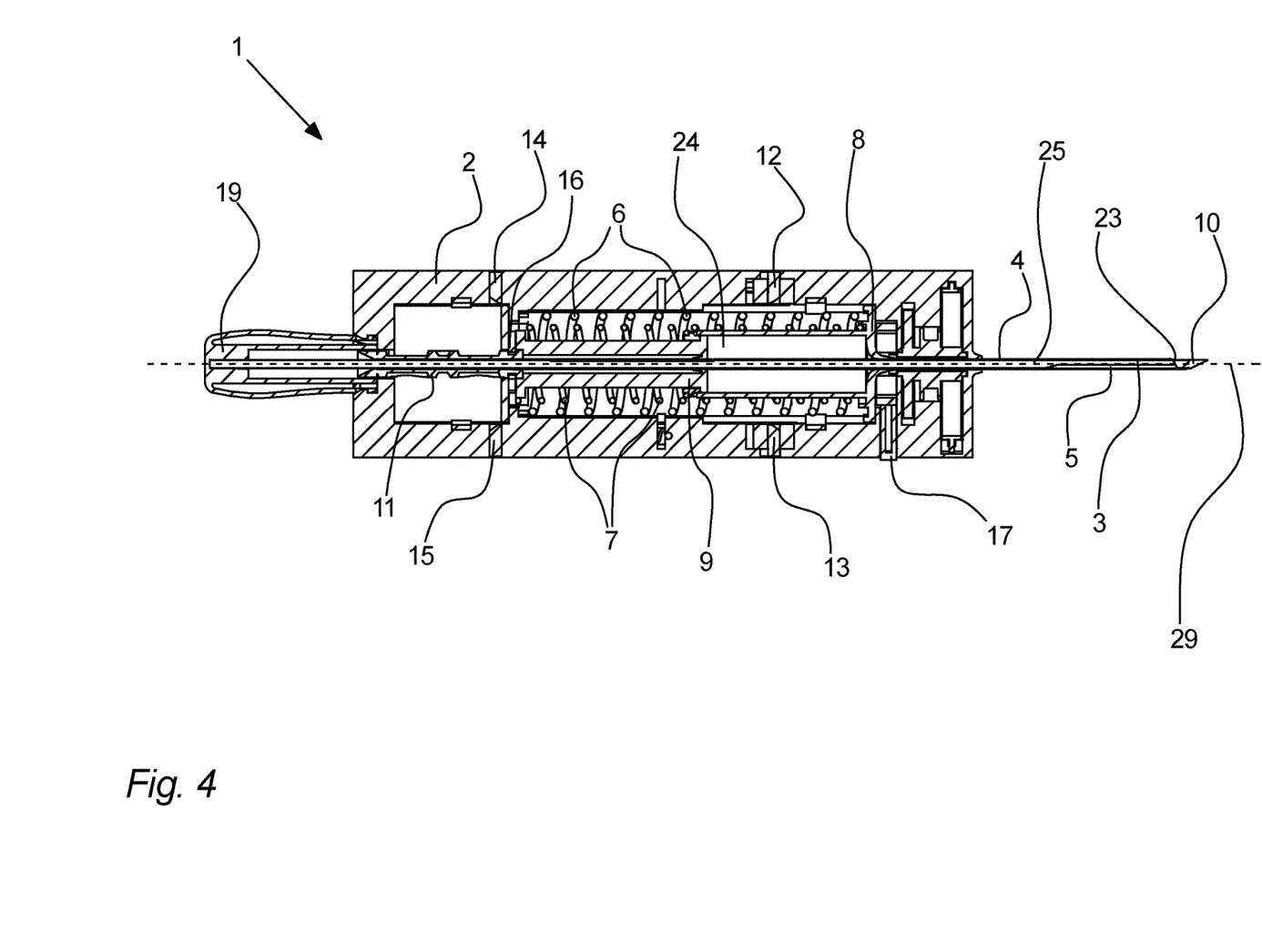
FIG. 4 illustrates a handheld device according to an embodiment of the invention.

Now, due to the pressure exerted by the cylinder 8 on the first and second pins 12, 13, the third and fourth pins 14, 15 are released, and the piston is free to move backwards, i.e. away from the beveled needle end 10 and towards the handle 19. The driving force for this movement is supplied by the second spring 7, which expands towards its equilibrium length. During this movement of the piston 9, the cylinder 8 is stationary, and the relative movement of the piston 9 and cylinder 8 away from each other expands the volume of the vacuum chamber 24, which results in a lower pressure in the vacuum chamber 24 and a suction in the needle arrangement 25. Furthermore, the outer cutting needle 4 moves with the piston 9, which means that the outer cutting needle 4 moves backwards relative to the inner sample extraction needle 3, thereby exposing and uncovering the side opening 5 of the inner sample extraction needle 3. Therefore, during this movement, the tissue sample chamber 26 is exposed, while the vacuum in the vacuum chamber 24 is gradually increased at the same time, causing soft material such as tissue 30 to be sucked into the tissue sample chamber 26. When this movement of the piston 9 and the outer cutting needle 4 driven by the expansion of the second spring 7 is completed, the configuration illustrated in a cross-sectional view on FIG. 3 is reached.

Now, the soft material such as tissue 30 surrounding the front end of the needle arrangement 25 extends through the side opening 5 into the tissue sample chamber 26. The first and second pins 12, 13 are retracted so as to release the cylinder 8. Due to the elastic driving force of the compressed first spring 6, the cylinder moves towards the beveled need end 10 of the control arrangement 2. Now, although the piston 9 is free to move back and forth in the cylinder 8, the piston 9 cannot leave the cylinder 8, e.g. due to an narrowing inner diameter of the cylinder 8 near its opening and a circular protrusion on the outside of the piston 9 near the end closest to the beveled needle end 10. Therefore, when the cylinder 8 moves towards the beveled needle end 10, the piston 9 and therefore also the outer cutting needle 4 moves with the cylinder 8, i.e. the piston 9 and cylinder 8 are stationary relative to each other, which again means that the vacuum in the vacuum chamber 24 is constant or at least substantially unaffected by the above described movement. Furthermore, the outer cutting needle 4 is connected and fixated to oscillation control arrangement 11, which move with the outer cutting needle 4 both for movements in a direction parallel to the longitudinal axis of the needle arrangement 25 and for rotations about the longitudinal axis 29 of the needle arrangement 25. The oscillation control arrangement 11 comprise on the outside a protruding ridge 20, which extends overall in a direction of the longitudinal axis 29 but which also rotates around the longitudinal axis 29 back and forth along the direction of the longitudinal axis 29. Thereby, the handheld device 1 reaches a configuration as shown in a cross-sectional view on FIG. 4.

Figure 6:
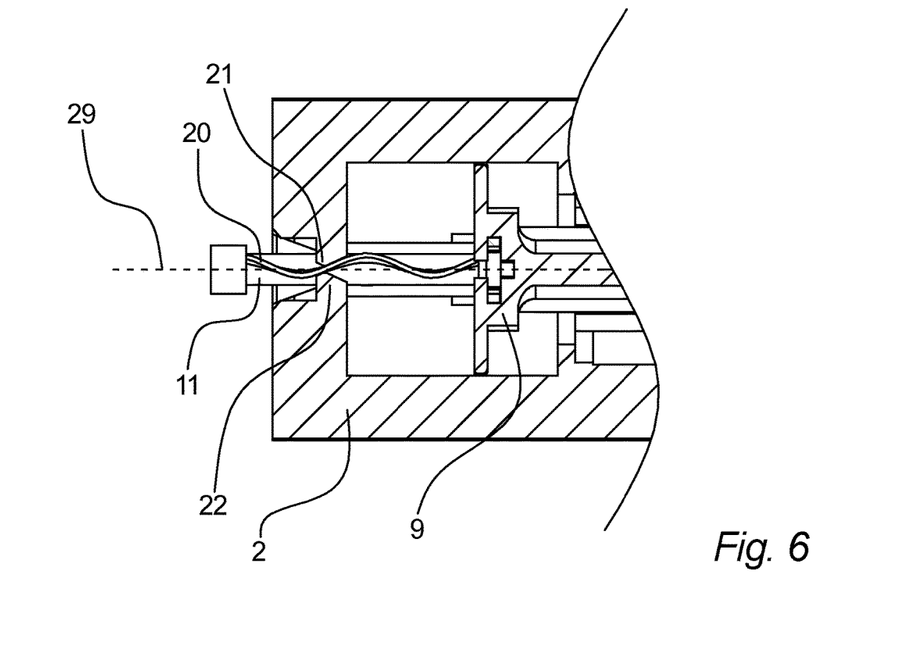
FIG. 6 illustrates oscillation control arrangement according to an embodiment of the invention.

The above described oscillation control arrangement 11 can be seen in a cross-sectional view on FIG. 6, where the oscillating ridge 20 can be seen to rotate in twice a first and twice in a second direction about the longitudinal axis 29 of the needle arrangement 25. Also, it can be seen on FIG. 6 that the net sum of the rotations is approximately zero, since the ridge 20 has the approximate same angular position in one end as the opposite end without rotating a fully around the longitudinal axis 29. In an example the ridge 20 may rotate e.g. 20° in a one direction about the longitudinal axis 29, then 20° in the opposite direction and then repeat this sequence once. In such an example, which may be close to the illustration on FIG. 6, the net sum of the rotations is substantially smaller than the sum of the numeric rotations, since the net sum is zero, while the sum of the numeric rotations is 80°. Furthermore, it can be seen on FIG. 6 that when the oscillation control arrangement 11 moves in a direction along the longitudinal axis 29 of the needle arrangement 25, the ridge 20 moves through a slit formed by a first protrusion 21 and a second protrusion 22. Therefore, during this movement, the first and second protrusions 21, 22 will force the oscillation control arrangement 11 to rotate about the longitudinal axis 29 of the needle arrangement 25, thereby facilitating an oscillatory rotation of the cutting needle 4, when it moves in a direction along the longitudinal axis 29 of the needle arrangement 25 due to the cutting needle 4 being connected and fixated to the oscillation control arrangement 11.

Figure 5:
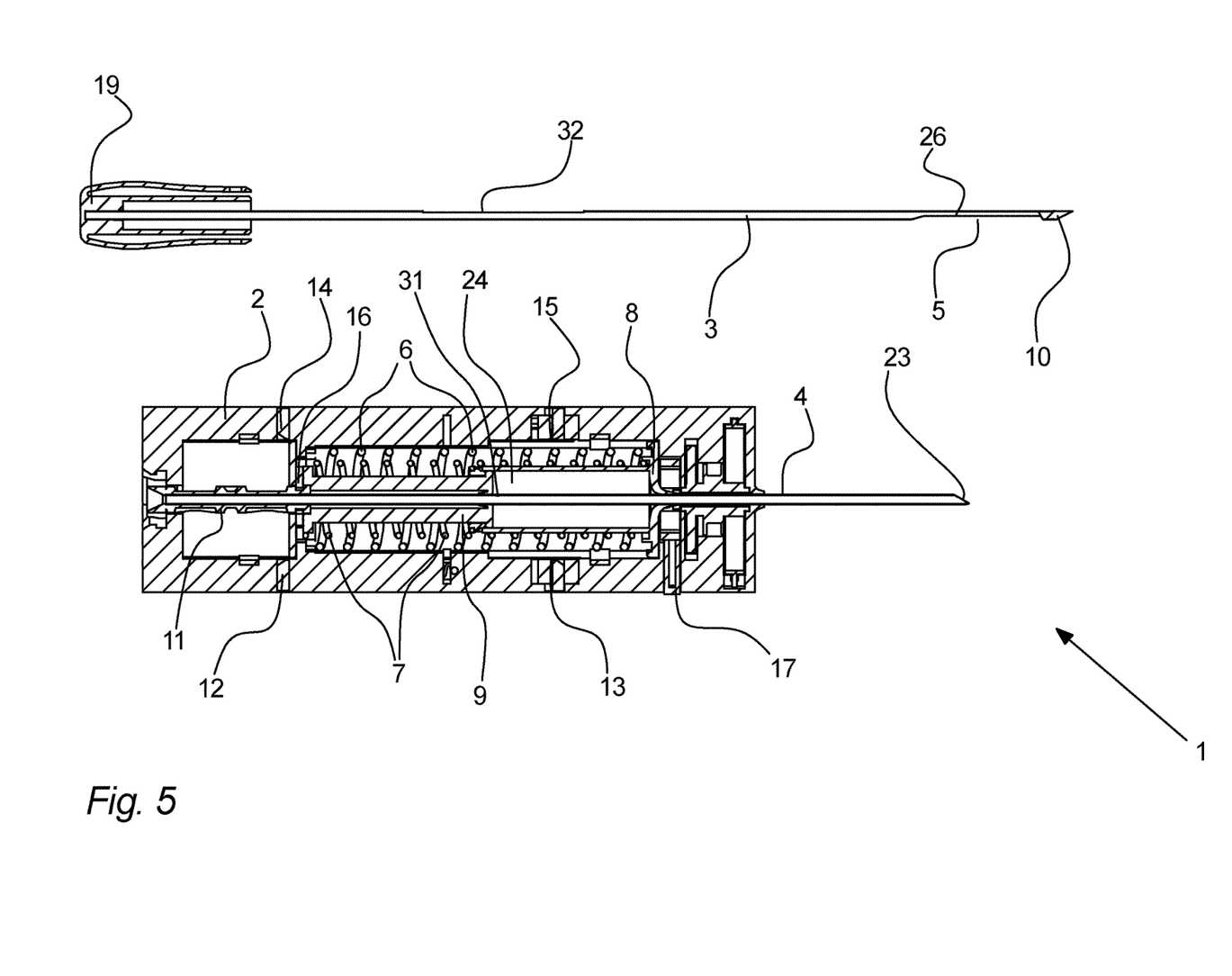
FIG. 5 illustrates a handheld device according to an embodiment of the invention.

Now, referring to FIG. 5, the handheld device 1 is shown in a cross-sectional view, where the sample extraction needle 3 is removed from the rest of the handheld device 1. Here the side opening 5 into the tissue sample chamber 26 can be observed. When a tissue sample 27 has been extracted by the handheld device, the sample extraction needle 3 can be removed as shown, and the tissue sample 27 can be removed, before the sample extraction needle 3 is inserted back into the handheld device 1, or, alternatively a new sample extraction needle 3 is inserted. This removal and reuse of the sample extraction needle 3 may be performed while the remaining cutting needle 4 remained inserted in the tissue 30. Thereby, multiple samples may be taken while only penetrating the skin once. In other words the handheld device is a single insertion, multiple samples device. Furthermore, a through-hole 31 can be seen in the cutting needle 4 and a slit 32 in the sample extraction needle 3. The through-hole 31 and slit 32 facilitate together fluid communication from the vacuum chamber 24 to the sample extraction needle 3.

Figure 7A:
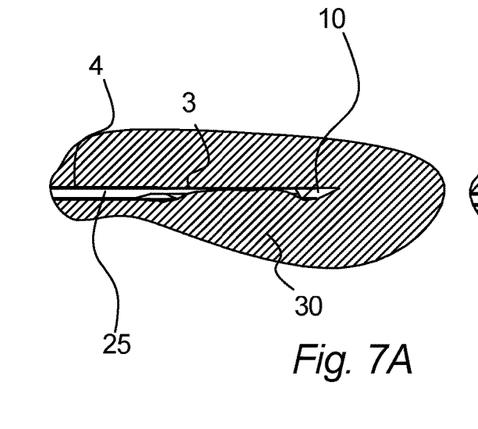
FIGS. 7A and 7B illustrate a tissue sample being extracted from tissue according to an embodiment of the invention.
Figure 7B:
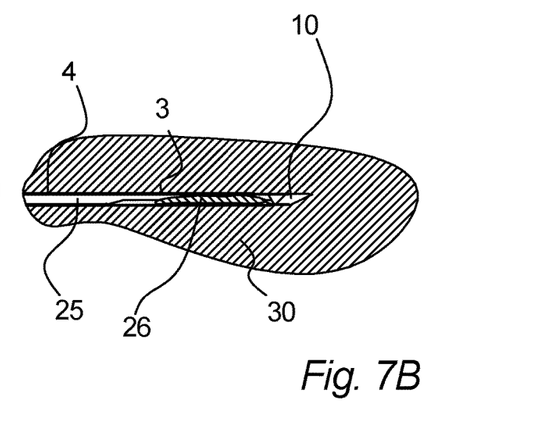

Now, on FIGS. 7A and 7B the extraction of a tissue sample 27 from the tissue 30 is illustrated. The needle arrangement 25 which is inserted into tissue 30 is seen in a cross-sectional view. On FIG. 7A, the cutting needle 4 has moved to exposed the side opening 5 of the sample extraction needle 3, thereby allowing tissue 30 to extend through this side opening 5 and into the tissue sample chamber 26. Furthermore, since the vacuum chamber 24 is in fluid communication with the sample extraction needle 3, the tissue 30 is sucked into the tissue sample chamber 26 due to this vacuum. Then the cutting needle 4 moves over the side opening 5 to a position illustrated on FIG. 7B, thereby cutting a tissue sample 26 from the tissue 30.

Figure 8:
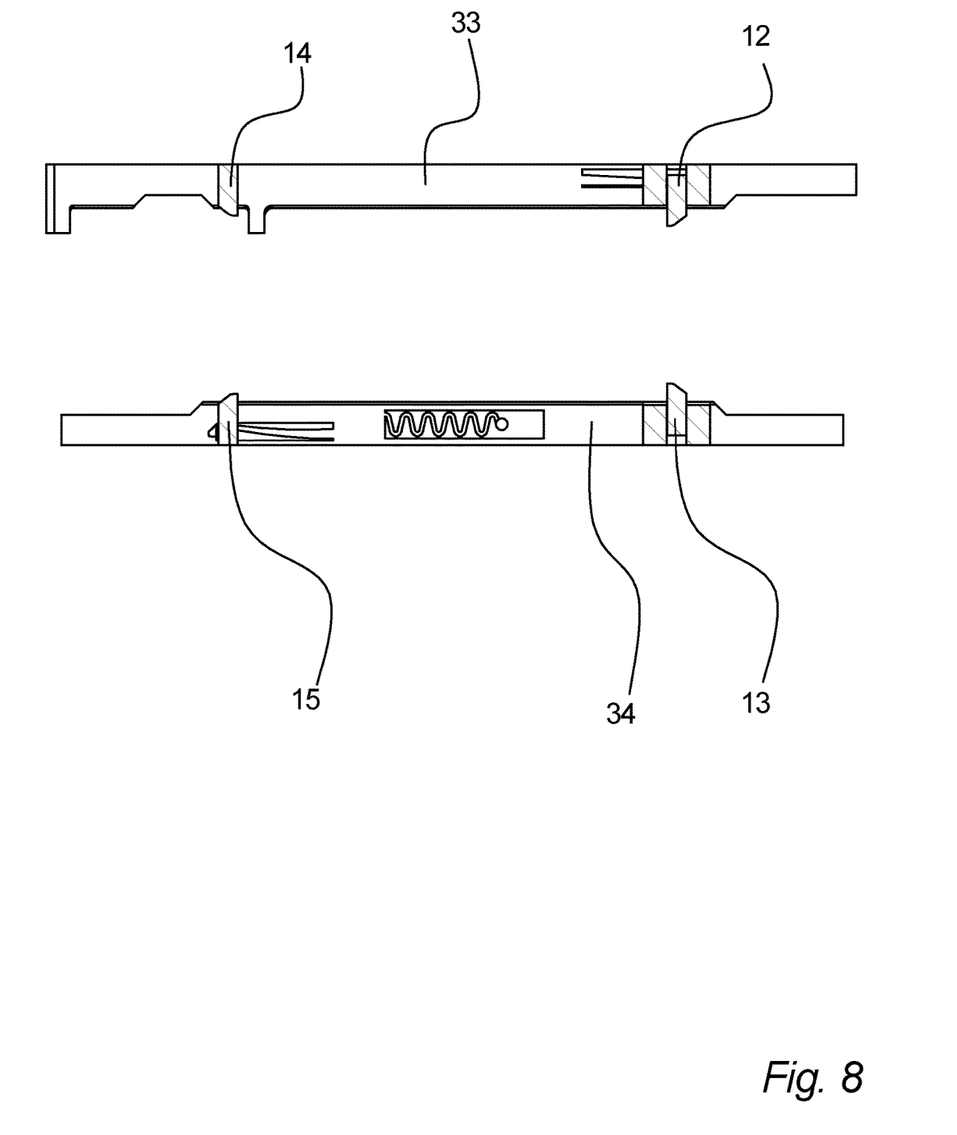
FIG. 8 illustrates pin control arrangements according to an embodiment of the invention.

Finally, on FIG. 8 illustrates pin control arrangements according to an embodiment of the invention. Here a first pin control arrangement 33 is shown connecting the first and third pins 12, 14. Also, a second pin control arrangement 34 is shown connecting the second and fourth pins 13, 15. The first and second pin control arrangements 33, 34 controls the action of the pins 12, 13, 14, 15, so that pressing the first and second pins 12, 13 to the right by a movement to the right of said second member causes the third and fourth pins 14, 15 to release the first member, causing this first member to move left. In other words, the pin control arrangements 33, 34 control the timing of the releasing of the first and second members to move according to the embodiments described in relation to FIGS. 1-7.

The invention has been exemplified above. However, it should be understood that the invention is not limited to the particular examples described above but may be designed and altered in a multitude of varieties within the scope of the invention as specified in the claims.

According to the present invention the embodiments mentioned in the specification of this patent application may be combined to obtain further embodiments according to the present invention.

LIST OF REFERENCE NUMERALS

1. Handheld device
2. Control arrangement
3. Sample extraction needle
4. Cutting needle
5. Side opening
6. First spring
7. Second spring
8. Cylinder
9. Piston
10. Beveled needle end
11. Oscillation control arrangement
12. First pin
13. Second pin
14. Third pin
15. Fourth pin
16. First connection arrangement
17. Start button
18. Ring
19. Sample extraction needle handle
20. Oscillation ridge
21. First protrusion
22. Second protrusion
23. Cutting edge
24. Vacuum chamber
25. Needle arrangement
26. Tissue sample chamber
27. Tissue sample
28. First end
29. Longitudinal axis
30. Tissue
31. Through-hole
32. Slit
33. First pin control arrangement
34. Second pin control arrangement

The invention claimed is:

1. A handheld device (1) for extraction of tissue samples (27), comprising a needle arrangement (25) and a control arrangement (2),
said needle arrangement (25) comprising:
a cutting needle (4), and
a sample extraction needle (3),
said needle arrangement (25) having a first end (28) for inserting into tissue (30),
said cutting needle (4) comprising:
a cutting edge (2) for cutting a tissue sample from said tissue (30),
said sample extraction needle (3) comprising:
a side opening (5) in fluid communication with a tissue sample chamber (26), wherein the side opening is for receiving said tissue sample,
wherein said cutting needle (4) is positioned relative to the sample extraction needle (3) so that the cutting needle (4) covers the side opening (5) in the sample extraction needle (3),
said control arrangement (2) comprising:
a housing that defines a space inside the housing;
a vacuum chamber (24) in fluid communication with said sample extraction needle (3), wherein the vacuum chamber (24) is defined by:
a first member in the space defined by the housing, and
a second member in the space defined by the housing,
wherein said first member and said second member are adapted to move relative to each other,
wherein said first member is in direct physical contact with and physically secured to said cutting needle (4) so that when the first member moves, the cutting needle (4) also moves with, and in the same manner as, the first member, and
a first spring (6) in the space defined by the housing,
a second spring (7) in the space defined by the housing,
wherein the first spring and the second spring are configured to urge the second member toward a first end of the housing of the control arrangement, and
pins configured to release the second member in response to a user initiating a tissue sample extraction cycle so that, when the second member is released, the second member moves, under influence from the first spring (6) and the second spring (7), relative to the first member and toward the first end of the housing of the control arrangement (2), while the first member remains stationary relative to the housing, thereby increasing a volume of, and building up vacuum in, the vacuum chamber (24),
wherein the sample extraction needle (3) and the cutting needle (4) are configured to remain stationary relative to each other while the second member moves toward the first end of the housing of the control arrangement (2) to build up vacuum in the vacuum chamber (24), so that the cutting needle (4)

continues to cover the side opening (5) in the sample extraction needle (3) while vacuum is being built up in the vacuum chamber (24), wherein the vacuum being built up in the vacuum chamber (24) extends to a tissue sample chamber (26) just inside the covered side opening (5) in the sample extraction needle (3) at a distal end of the sample extraction needle (3) close to a cutting tip of the sample extraction needle (3), wherein said handheld device (1) is further configured so that a further movement between said first member and said second member to continue increasing the volume of said vacuum chamber (24) after the vacuum has been built up in the vacuum chamber (24) and in the tissue sample chamber (26) will cause said cutting needle (4) to move relative to said sample extraction needle (3) to a position such that the cutting needle (4) no longer covers the side opening (5) of said sample extraction needle (3), wherein the tissue sample chamber 26 is located at a distal end of the sample extraction needle close to a tip of the sample extraction needle.

2. A handheld device (1) according to claim 1, wherein said first member is a piston (9) and said second member is a cylinder (8).

3. A handheld device (1) according to claim 1, wherein said first member is a cylinder (8) and said second member is a piston (9).

4. A handheld device (1) according to claim 1, wherein said movement between said first member and said second member to increase the volume of said vacuum chamber (24) is in a direction along a longitudinal axis (29) of the needle arrangement (25).

5. A handheld device (1) according to claim 1, wherein the vacuum chamber (24) surrounds at least a part of said needle arrangement (25).

6. A handheld device (1) according to claim 5, wherein the vacuum chamber (24) is centered about the longitudinal axis (29) of the needle arrangement (25).

7. A handheld device (1) according to claim 1, wherein the cutting needle (4) is an outer needle surrounding the sample extraction needle (3) being an inner needle.

8. A handheld device (1) according to claim 1, wherein said cutting needle (4) has a beveled end (10).

9. A handheld device (1) according to claim 1, wherein said second member is adapted to perform a movement along a longitudinal axis (29) of the needle arrangement (25) towards the first end (28) of the needle arrangement (25) thereby increasing the volume of the vacuum chamber (24) and building up the vacuum before the side opening (5) is exposed.

10. A handheld device (1) according to claim 1, wherein said first and second members are adapted to move together in a direction along a longitudinal axis (29) of the needle arrangement (25) in a direction towards the first end (28) of the needle arrangement (25) while being stationary relative to each other, wherein said cutting needle (4) connected to said first member and said sample extraction needle (3) are adapted for moving relative to each other along the longitudinal axis (29) of said needle arrangement (25) from a first relative position to a second relative position, wherein at least a part of said side opening (5) is exposed in said first relative position, and wherein said side opening (5) of said sample extraction needle (3) is substantially covered in said second relative position, thereby cutting said tissue sample (27) from said tissue (30).

11. A handheld device (1) according to claim 10, wherein said movement from said first relative position to said second relative position comprises an oscillatory rotation of said cutting needle (4) relative to said sample extraction needle (3) about the longitudinal axis (29) of the needle arrangement (25), where said oscillatory rotation comprises at least a first relative rotation and a second relative rotation, where the first and second relative rotations have different oscillatory velocities.

12. A handheld device (1) according to claim 10, wherein said movement from said first relative position to said second relative position comprises an oscillatory rotation of said cutting needle (4) relative to said sample extraction needle (3) about the longitudinal axis (29) of the needle arrangement (25), where said oscillatory rotation comprises at least a first relative rotation and a second relative rotation, where the first and second relative rotations have opposite rotational directions.

13. A handheld device (1) according to claim 10, wherein the handheld device (1) comprises a vacuum removal arrangement for removing the vacuum when said cutting needle (4) has reached the second relative position, thereby substantially covering said side opening (5) of said sample extraction needle (3).

14. A handheld device (1) according to claim 13, wherein the vacuum removal arrangement comprises a valve.

15. A handheld device (1) according to claim 1, wherein the control arrangement (2) furthermore comprises a charging arrangement for charging a first driving arrangement and said second driving arrangement.

16. A handheld device (1) according to claim 15, wherein the charging arrangement is a ring (18) and a string.

17. A handheld device (1) according to claim 1, wherein the sample extraction needle (3) may be removed from the rest of the handheld device (1) so as to remove extracted tissue samples (27).

18. A handheld device (I) according to claim 1, wherein the sample extraction needle (3) is inside the cutting needle (4).

19. A handheld device for extraction of tissue samples, the handheld device comprising:

a control arrangement comprising a housing that defines a space inside the housing; and a needle arrangement, a portion of which extends from a first end of the housing of the control arrangement, wherein a distal end of the portion of the needle arrangement that extends from the first end of the control portion is configured for inserting into tissue, the needle arrangement comprising:

an inner hollow sample extraction needle configured to define a beveled distal end and an opening in a side surface of the inner hollow sample extraction needle, wherein the opening opens into a tissue sample chamber inside the inner hollow sample extraction needle, wherein the opening in the side surface of the inner hollow sample extraction needle is separated from the beveled distal end of the hollow sample extraction needle by a distance; and an outer hollow cutting needle that is outside the inner hollow sample extraction needle and configured to define a cutting edge at a distal end of the outer hollow cutting needle, wherein the outer hollow cutting needle extends over and covers the opening in the side of the surface of the inner hollow sample extraction needle, the control arrangement further comprising:
- a cylinder in the space inside the housing;
- a piston inside the cylinder;
- a first spring in the space inside the housing, wherein the first spring is tensioned to urge the cylinder toward the first end of the housing;
- a second spring in the space inside the housing, wherein the second spring is tensioned to urge the cylinder toward the first end of the housing, and to urge the piston toward a second end of the housing that is opposite the first end of the housing;
- a first set of pins configured to prevent the cylinder from moving under the urging of the first spring toward the first end of the housing until a user initiates a tissue sample extraction cycle, which causes the first set of pins to release the cylinder to move toward the first end of the housing;
- a second set of pins that extend from the housing into the space inside the housing and that are retractable from the space into the housing, wherein the second set of pins are closer to the first end of the housing than the first set of pins; and
- a third set of pins that extend from the housing into the space inside the housing to prevent the piston from moving under the urging of the second spring toward the second end of the housing, wherein the third set of pins are retractable from the space into the housing, wherein the inner hollow sample extraction needle is physically supported by the handheld device so that an axial position of the hollow sample extraction needle is fixed and remains fixed relative to the housing of the control arrangement, and wherein the outer hollow cutting needle is in direct physical contact with and physically secured to the piston so that when the piston moves the outer hollow cutting needle also moves, with and in the same manner as the piston.

20. The handheld device according to claim 19, wherein the cylinder, the piston, the inner hollow sample extraction needle, and the outer hollow cutting needle share a common axis.

* * * * *